United States Patent [19]
Cohan et al.

[11] Patent Number: 6,114,367
[45] Date of Patent: Sep. 5, 2000

[54] ISOXAZOLINE COMPOUNDS AS INHIBITORS OF TNF RELEASE

[75] Inventors: Victoria Lee Cohan, East Lyme; Edward Fox Kleinman, Stonington, both of Conn.

[73] Assignee: Pfizer Inc, New York, N.Y.

[21] Appl. No.: 09/187,833

[22] Filed: Nov. 6, 1998

Related U.S. Application Data

[60] Division of application No. 08/700,431, filed as application No. PCT/IB95/00078, Feb. 3, 1995, Pat. No. 5,869,511, which is a continuation-in-part of application No. 08/209,125, Mar. 9, 1994, abandoned.

[51] Int. Cl.[7] ............................. A61K 31/42; A61K 31/47
[52] U.S. Cl. ............................ 514/378; 514/380; 514/307
[58] Field of Search ..................................... 514/378, 380, 514/307

[56] References Cited

FOREIGN PATENT DOCUMENTS 0026928  4/1981  European Pat. Off. ...... C07D 261/08
0012038  8/1980  Japan ............................. A61K 31/42

OTHER PUBLICATIONS

Spooner et al, Clinical Immunology & Immunopathology vol. 62(1) pp. S11–S17, 1992.
Brennan et al, Lancet Jul. 29, 1989 pp. 244–247.

*Primary Examiner*—Russell Travers
*Attorney, Agent, or Firm*—Peter C. Richardson; Gregg C. Benson; Carl J. Goddard

[57] ABSTRACT

This invention relates to isoxazoline compounds which are inhibitors of tumor necrosis factor (TNF). The isoxazoline compounds are useful for inhibiting TNF in a mammal in need thereof and in the treatment or alleviation of inflammatory conditions or disease, including but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, graft versus host disease and cachexia associated with AIDS or cancer. This invention also relates to pharmaceutical compositions useful therefor comprising such compounds.

16 Claims, No Drawings

ISOXAZOLINE COMPOUNDS AS INHIBITORS OF TNF RELEASE

This is a division of application Ser. No. 08/700,431, filed on Sep. 5, 1996, now U.S. Pat. No. 5,869,511 which is the national stage of International Application No. PCT/IB95/00078, filed Feb. 3, 1995 which is a continuation-in-part of U.S. Ser. No. 08/209,125, filed Mar. 9, 1994, now abandoned.

BACKGROUND OF THE INVENTION

This invention relates to a method of inhibiting production of TNF (tumor necrosis factor) in a mammal in need thereof which method comprises administering to said mammal an effective amount of a compound of the formula (I) (shown below) or a pharmaceutically acceptable salt thereof, which, as such are also useful in the treatment or alleviation of inflammatory conditions or disease including, but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, graft versus host disease and cachexia associated with AIDS or cancer; and this invention also relates to pharmaceutical compositions useful therefor.

TNF is produced by monocytes/macrophages and has a variety of biological activities relevant to the pathogenesis of rheumatoid arthritis (RA) and osteoarthritis (OA). Firstly, TNF can promote the accumulation of all leukocyte types by stimulating the endothelium to express adhesion molecules (T. H. Pohlman et al., *J. Immunol.,* 136, pp. 4548–4553, 1986) and to release secondary chemotactic cytokines such as interleukin 8 (R. M. Strieter et al., *Science,* 243, pp. 1467–1469, 1989). Secondly, TNF can stimulate cells within the joint to synthesize and express the inducible cyclooxygenase enzyme (COX 2) and the inducible NO synthase. The products of these enzymes, prostaglandins and NO, are important mediators of pain and inflammation. Thirdly, and perhaps most importantly, TNF, like IL-1, can activate chondrocytes to degrade their own extracellular matrix and suppress synthesis of cartilage matrix components leading to cartilage destruction. In addition to these effects, TNF plays a pivotal role in the regulation of the production of other cytokines. This has been demonstrated in cultures of dissociated RA synovial cells where blocking the activity of TNF can inhibit the secretion of IL-1 (F. M. Brennan et al., *Lancet,* 2, pp. 244–247, 1989). Thus, blocking TNF production should prevent the synthesis of other downstream cytokines such as IL-1. Finally, TNF has been immunolocalised in both RA and OA synovial membranes(M. N. Farahat et al., *Ann. Rheum. Dis.,* 52, pp. 870–875, 1993).

TNF is recognized to be involved in many infectious and auto-immune diseases (W. Fiers, *FEBS Letters,* 1991, 285, p. 199). Furthermore, it has been shown that TNF is the prime mediator of the inflammatory response seen in sepsis and septic shock (C. E. Spooner et al., *Clinical Immunology and Immunopathology,* 1992, 62, p. S11).

The compounds utilized in the present invention are disclosed and claimed in co-pending PCT Application Number PCT/IB94/00333 filed Oct. 26, 1994 and PCT Application Number PCT/IB94/00313 filed Oct. 12, 1994, both of which are assigned to the assignee hereof, and wherein said compounds are disclosed as having phosphodiesterase type IV ($PDE_{IV}$) inhibiting activity. The teachings thereof are incorporated herein by reference.

SUMMARY OF THE INVENTION

This invention is concerned with a method of inhibiting production of TNF (tumor necrosis factor) in a mammal in need thereof which method comprises administering to said mammal an effective amount of a compound selected from the group consisting of compounds of the formula (I)

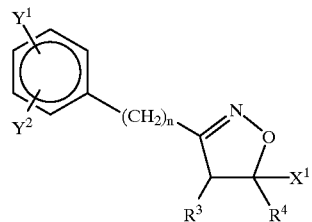

the racemic, racemic-diastereomeric mixtures and optical isomers of said compounds, and the pharmaceutically acceptable salts thereof, wherein $X^1$ is —$(CH_2)_qOH$, —$CHOHR^5$ or —$(CH_2)_mCON(R^6)$(OH);
  wherein q and m are each independently 0 or an integer from 1 to 5; $R^5$ is ($C_1$–$C_4$)alkyl; and $R^6$ is hydrogen or ($C_1$–$C_3$)alkyl;

n is 0, 1, 2 or 3;

$Y^1$ and $Y^2$ are independently selected from the group consisting of hydrogen, ($C_1$–$C_6$)alkyl, optionally substituted phenylalkyl having 1 to 6 carbons in the alkyl portion, optionally substituted phenoxyalkyl having 1 to 6 carbons in the alkyl portion, ($C_3$–$C_7$)cycloalkyl, difluoromethyl, trifluoromethyl, fluoro, chloro, bromo, iodo, —$OR^1$ and —$OR^2$;
  wherein the aromatic portion of the optionally substituted phenylalkyl, and the aromatic portion of the optionally substituted phenoxyalkyl are optionally independently substituted with ($C_1$–$C_4$)alkyl, ($C_1$–$C_4$)alkoxy, halogen or $CF_3$;
  $R^1$ is ($C_1$–$C_5$)alkyl, phenylalkyl having one to four carbon atoms in the alkyl portion, fluoromethyl, difluoromethyl, trifluoromethyl, or —$(CH_2)_r$-quinoline wherein r is 0 or an integer from 1 to 5;
  $R^2$ is ($C_1$–$C_3$)alkyl, ($C_3$–$C_7$)cycloalkyl, alkoxyalkyl having 3 to 7 carbons in the alkoxy portion and 2 to 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;
    wherein the aromatic portion of the optionally substituted phenylalkyl, the aromatic portion of the optionally substituted phenoxyalkyl and the optionally substituted indanyl are optionally substituted with ($C_1$–$C_4$)alkyl, ($C_1$–$C_4$)alkoxy, halogen or $CF_3$;

$R^3$ is hydrogen, ($C_1$–$C_3$)alkyl, fluoro($C_1$–$C_3$)alkyl having 1 to 3 fluoro atoms, mono-hydroxyalkyl having 1 to 3 carbons or alkoxyalkyl having 1 to 3 carbons in the alkyl portion and 1 to 3 carbons in the alkoxy portion;

$R^4$ is hydrogen, ($C_1$–$C_5$)alkyl, fluoro($C_1$–$C_5$)alkyl having 1 to 3 fluoro atoms, mono-hydroxyalkyl having 1 to 3 carbons, phenyl, alkoxyalkyl having 1 to 3 carbons in the alkyl portion and 1 to 3 carbons in the alkoxy portion, aminoalkyl having 1 to 3 carbons,

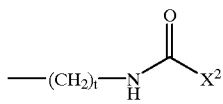

wherein $X^2$ is $(C_1-C_3)$alkyl and t is an integer from 1 to 3, N-alkylaminoalkyl having 1 to 3 carbons in the alkylamino portion and 1 to 3 carbons in the alkyl portion, $(C_3-C_7)$ cycloalkyl or N,N-dialkylaminoalkyl having a total of 2 to 6 carbons in the dialkylamino portion and 1 to 3 carbons in the alkyl portion;

or $R^3$ and $R^4$ are taken together with the carbon atoms to which they are attached and form a carbocyclic ring having 4 to 7 carbon atoms.

This invention is further directed to a method of treating or alleviating sepsis, septic shock, inflammatory bowel disease, tuberculosis, graft versus host disease or cachexia associated with AIDS or cancer in a mammal in need thereof which method comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$, $Y^2$, n, $R^3$, $R^4$ and $X^1$ are as defined hereinabove for formula (I).

Further, this invention provides a method of treating or alleviating an inflammatory disease or condition, said inflammatory disease or condition comprising rheumatoid arthritis, osteoarthritis, asthma, bronchitis, chronic obstructive airways disease, psoriasis, allergic rhinitis, or dermatitis, in a mammal in need thereof which method comprises administering to said mammal an effective amount of a compound selected from the group of compounds of the formula (I), as shown above, the racemic, racemic-diastereomeric mixtures and optical isomers of said compounds, and the pharmaceutically acceptable salts thereof, wherein $X^1$ is $—(CH_2)_qOH$ or $—CHOHR^5$ where q is 0 or an integer from 1 to 5 and $R^5$ is $(C_1-C_4)$alkyl; and $Y^1$, $Y^2$, n, $R^3$ and $R^4$ are as first defined hereinabove for formula (I).

Furtherstill, this invention provides pharmaceutical compositions comprising a pharmaceutically acceptable diluent or carrier and a TNF inhibiting amount of a compound selected from the group consisting of compounds of the formula (I), as shown above, the racemic, racemic-diastereomeric mixtures and optical isomers of said compounds, and the pharmaceutically acceptable salts thereof, wherein $Y^1$, $Y^2_1$ n, $R^3$, $R^4$ and $X^1$ are as first defined hereinabove for formula (I).

A preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is $—OR^1$ and is attached to the 4-position of the phenyl ring; $Y^2$ is $—OR^2$ and is attached to the 3-position of the phenyl ring and n, $R^1$, $R^2$, $R^3$, $R^4$ and $X^1$ are as first defined above for formula (I).

Another preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is methoxy or $—OCH_2$-2-quinoline and is attached to the 4-position of the phenyl ring; $Y^2$ is hydrogen, cyclopentyloxy or $—O(CH_2)_5$ phenyl and is attached to the 3-position of the phenyl ring; $R^3$ is hydrogen, methyl or ethyl; $R^4$ is hydrogen, methyl or ethyl; $X^1$ is $—(CH_2)_qOH$, or $—CH(OH)CH_3$ wherein q is 0, 1 or 2; and n is 0.

Yet another preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is $—OCH_2$-2-quinoline and is attached to the 4-position of the phenyl ring; $Y^2$ is hydrogen or $—O(CH_2)_5$phenyl and is attached to the 3-position of the phenyl ring; $R^3$ is hydrogen, methyl or ethyl; $R^4$ is ethyl; $X^1$ is $—CONHOH$; and n is 0.

A more preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is $—OR^1$ and is attached to the 4-position of the phenyl ring, where $R^1$ is $(C_1-C_4)$alkyl, phenylalkyl having one to four carbon atoms in the alkyl portion or $—(CH_2)_r$-quinoline; $Y^2$ is $—OR^2$ and is attached to the 3-position of the phenyl ring; $X^1$ is $—(CH_2)_mCON(R^6)(OH)$; n is 0; and m, r, $R^2$, $R^3$, $R^4$ and $R^6$ are as first defined above for formula (I).

Another more preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is $—OR^1$ and is attached to the 4-position of the phenyl ring, where $R^1$ is $(C_1-C_4)$alkyl, phenylalkyl having one to four carbon atoms in the alkyl portion or $—(CH_2)_r$-quinoline; $Y^2$ is $—OR^2$ and is attached to the 3-position of the phenyl ring, where $R^2$ is phenylalkyl having 1 to 6 carbons in the alkyl portion, $(C_3-C_7)$cycloalkyl or $(C_1-C_3)$alkyl; $X^1$ is $—(CH_2)_mCON(R^6)(OH)$; m is 0; n is 0; and r, $R^3$, $R^4$ and $R^6$ are as first defined above for formula (I).

An even more preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is $—OR^1$ and is attached to the 4-position of the phenyl ring, where $R^1$ is $(C_1-C_4)$alkyl, phenylalkyl having one to four carbon atoms in the alkyl portion or $—(CH_2)_r$-quinoline; $Y^2$ is $—OR^2$ and is attached to the 3-position of the phenyl ring, where $R^2$ is 5-phenylpentyl, benzyl, cyclopentyl or methyl; $X^1$ is $—(CH_2)_mCON(R^6)(OH)$; m is 0; n is 0; and r, $R^3$, $R^4$ and $R^6$ are as first defined above for formula (I).

A particularly preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is —$OR^1$ and is attached to the 4-position of the phenyl ring, where $R^1$ is ($C_1$–$C_4$)alkyl, phenylalkyl having one to four carbon atoms in the alkyl portion or —$(CH_2)_r$-quinoline; $Y^2$ is —$OR^2$ and is attached to the 3-position of the phenyl ring, where $R^2$ is 5-phenylpentyl, benzyl, cyclopentyl or methyl; $X^1$ is —$(CH_2)_m CON(R^6)(OH)$; m is 0; n is 0; $R^3$ is hydrogen and r, $R^4$ and $R^6$ are as first defined above for formula (I).

Another particularly preferred method of inhibiting production of TNF in a mammal in need thereof comprises administering to said mammal an effective amount of a compound selected from the group consisting of compounds of the formula (I), as shown above, the racemic, racemic-diastereomeric mixtures and optical isomers of said compounds, and the pharmaceutically acceptable salts thereof, wherein $Y^1$ is —$OR^1$ and is attached to the 4-position of the phenyl ring, where $R^1$ is ($C_1$–$C_4$)alkyl, phenylalkyl having one to four carbon atoms in the alkyl portion or —$(CH_2)_r$-quinoline; $Y^2$ is —$OR^2$ and is attached to the 3-position of the phenyl ring, where $R^2$ is 5-phenylpentyl, benzyl, cyclopentyl or methyl; $X^1$ is —$(CH_2)_m CON(R^6)(OH)$; m is 0; n is 0; $R^3$ is hydrogen; $R^4$ is hydrogen or ($C_1$–$C_5$)alkyl and r and $R^6$ are as first defined above for formula (I).

More particularly preferred methods of inhibiting production of TNF in a mammal in need thereof comprise administering to said mammal an effective amount of (1) a compound selected from the group consisting of compounds of the formula (I), as shown above, the racemic, racemic-diastereomeric mixtures and optical isomers of said compounds, and the pharmaceutically acceptable salts thereof, wherein $Y^1$ is —$OR^1$ and is attached to the 4-position of the phenyl ring, where $R^1$ is ($C_1$–$C_4$)alkyl, phenylalkyl having one to four carbon atoms in the alkyl portion or —$(CH_2)_r$-quinoline, where r is as first defined above for formula (I); $Y^2$ is $OR^2$ and is attached to the 3-position of the phenyl ring, where $R^2$ is 5-phenylpentyl, benzyl, cyclopentyl or methyl; $X^1$ is —$(CH_2)_m CON(R^6)(OH)$; m is 0; n is 0; $R^3$ is hydrogen; $R^4$ is hydrogen or ($C_1$–$C_5$)alkyl and $R^6$ is hydrogen or ($C_1$–$C_3$)alkyl; or (2) a compound or the pharmaceutically acceptable salt thereof of the formula (I) as shown above, the racemic, racemic-diastereomeric mixtures and optical isomers of said compounds, and the pharmaceutically acceptable salts thereof, wherein $Y^1$ is —$OR^1$ and is attached to the 4-position of the phenyl ring, where $R^1$ is methyl; $Y^2$ is —$OR^2$ and is attached to the 3-position of the phenyl ring, where $R^2$ is cyclopentyl; $X^1$ is —$(CH_2)_m CON(R^6)(OH)$; m is 0; n is 0; $R^3$ is hydrogen; $R^4$ is hydrogen; and $R^6$ is hydrogen; or (3) the levorotatory (negative rotation) isomer of a compound or the pharmaceutically acceptable salt thereof of the formula (I) as shown above, wherein $Y^1$ is —$OR^1$ and is attached to the 4-position of the phenyl ring, where $R^1$ is methyl; $Y^2$ is —$OR^2$ and is attached to the 3-position of the phenyl ring, where $R^2$ is cyclopentyl; $X^1$ is —$(CH_2)_m CON(R^6)(OH)$; m is 0; n is 0; $R^3$ is hydrogen; $R^4$ is hydrogen; and $R^6$ s hydrogen.

Other more particularly preferred methods of inhibiting production of TNF in a mammal in need thereof comprise administering to said mammal an effective amount of (1) a compound selected from the group consisting of compounds of the formula (I), as shown above, the racemic, racemic-diastereomeric mixtures and optical isomers of said compounds, and the pharmaceutically acceptable salts thereof, wherein $Y^1$ is —$OR^1$ and is attached to the 4-position of the phenyl ring, where $R^1$ is methyl; $Y^2$ is —$OR^2$ and is attached to the 3-position of the phenyl ring, where $R^2$ is cyclopentyl; $X^1$ is —$(CH_2)_m CON(R^6)(OH)$; m is 0; n is 0; $R^3$ is hydrogen; $R^4$ is methyl; and $R^6$ is hydrogen; or (2) the levorotatory (negative rotation) isomer of a compound or the pharmaceutically acceptable salt thereof of the formula (I) as shown above, wherein $Y^1$ is —$OR^1$ and is attached to the 4-position of the phenyl ring, where $R^1$ is methyl; $Y^2$ is —$OR^2$ and is attached to the 3-position of the phenyl ring, where $R^2$ is cyclopentyl; $X^1$ is —$(CH_2)_m CON(R^6)(OH)$; m is 0; n is 0; $R^3$ is hydrogen; $R^4$ is methyl; and $R^6$ is hydrogen.

DETAILED DESCRIPTION OF THE INVENTION

The compounds utilized in the methods of the present invention, which are selected from the group consisting of compounds of the formula (I), as first defined above, the racemic, racemic-diastereomeric mixtures and optical isomers thereof and the pharmaceutically acceptable salts thereof, are readily and generally prepared by the following reaction processes.

Compounds of the formula (I) wherein $X^1$ is —$(CH_2)_q OH$ wherein q is 1 to 5 and $R^4$ is alkyl having 1 to 5 carbon atoms, are synthesized by reducing the corresponding ester, wherein $X^1$ is an alkyl ester, with diisobutylaluminum hydride (DIBAL-H) according to the following procedure. A compound of formula (I) wherein $X^1$ is a methyl or ethyl ester, is dissolved in THF and chilled to about −78° C. Approximately 2 to 4 equivalents of DIBAL-H in hexane is added to the cold THF mixture. The solution is warmed to about −30° C. and then quenched with a dilute solution of HCl. The reaction is worked-up according to methods well known to those skilled in the art.

Alternatively, the compounds of formula (I) wherein $X^1$ is hydroxymethyl and $R^4$ is hydrogen, are synthesized by reducing a compound of formula (I) wherein $X^1$ is an aldehyde. The aldehyde compound is dissolved in an alcoholic solvent and treated with sodium borohydride; the mixture is stirred at room temperature until the reaction is substantially complete. Further, the compounds of formula (I) wherein $X^1$ is 1-hydroxyalkyl (i.e., —CH(OH)alkyl) are synthesized by reducing a corresponding compound of formula (I) wherein $X^1$ is a ketone moiety (i.e, —CO-alkyl) according to the following procedure. The corresponding ketone compound of formula (I) is dissolved in an alcoholic solvent and cooled to about 0° C., to which is added sodium borohydride. The mixture is stirred until the bubbling ceases and then stirred at room temperature for approximately 1 hour. The reaction is worked-up according to methods well known to those skilled in the art.

Compounds of the formula (I) wherein $X^1$ is hydroxy (that is when q=0) can be synthesized by dissolving the corresponding acyloxy derivative, such as when $X^1$ is —$OCOCH_3$, in an alcoholic solvent and treating the solution with approximately 1.1 equivalents of sodium methoxide. The reaction mixture is stirred at room temperature until the reaction is substantially complete, which is usually about 1 hour. The reaction is worked-up according to methods well known to those skilled in the art.

The compounds of the formula (I) wherein $X^1$ is —$(CH_2)_m CON(R^6)(OH)$ are readily synthesized by the following method. To an alcoholic solution of sodium methoxide is added an alcoholic solution of the appropriate hydroxylamine hydrochloride and a compound of the formula

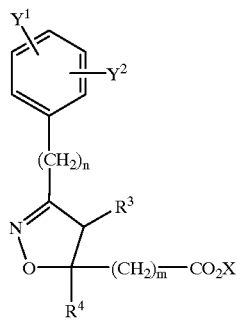

wherein X is an alkyl group and $Y^1$, $Y^2$, $R^3R^4$, m and n are as defined for formula (I). The reaction mixture is stirred for about 12 to 24 hours, preferably 16 hours, at room temperature. The solvent is evaporated and the residue is worked-up according to methods well known to those skilled in the art. The intermediate ester compounds of the formula

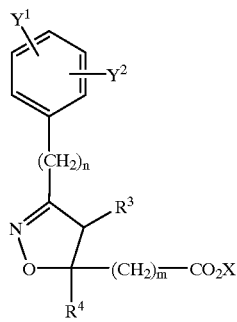

wherein $Y^1$, $Y^2$, $R^3$, $R^4$, m and n are as defined above for the compound of formula (I), and X is an alkyl group, are synthesized according to the following procedure. To a mixture of N-chlorosuccinimide and pyridine in an inert solvent, such as methylene chloride, is added an oxime of the formula

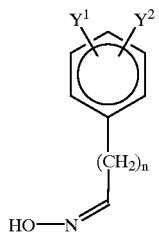

wherein $Y^1$, $Y^2$ and n are as defined above for formula (I). The mixture is allowed to stir for about 2 to 5 hours, preferably about 2 hours. A compound of the formula,

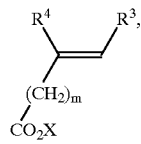

wherein $R^3$, $R^4$ and m are as defined above for formula I and X is an alkyl group, is added followed by the addition of triethylamine to the mixture and the mixture stirred for about 2 hours more at room temperature. The reaction is worked up according to methods well known to those skilled in the art.

As ascertained by one skilled in the art enabled by this disclosure, pharmaceutically-acceptable acid addition salts of certain compounds utilized in the present invention can be prepared which include, but are not limited to, those formed with HCl, HBr, $HNO_3$, $H_2SO_4$, $H_3PO_4$, $CH_3SO_3H$, $p\text{-}CH_3C_6H_4SO_3H$, $CH_3CO_2H$, gluconic acid, tartaric acid, maleic acid and succinic acid.

The ability of the compounds or the pharmaceutically acceptable salts thereof to inhibit TNF and, consequently, demonstrate their effectiveness for treating inflammatory conditions and diseases is shown by the following in vitro assay.

Lipopolysaccharide (LPS)-Induced TNF Release
From Human Monocytes

Human Peripheral Blood Monocytes

Venous blood from healthy volunteers is collected in EDTA. Monocytes are separated by ficoll-hypaque and washed three times in complete HBSS (Hanks Balanced Salt Solution, available from GIBCO, Grand Island, N.Y.). Cells are resuspended in a final concentration of $1.3 \times 10^6$ cells per mL in pre-warmed RPMI (available from GIBCO, Grand Island, N.Y.) (containing 5% fetal calf serum, glutamine, penicillin/streptomycin antibiotic and nystatin (all available from GIBCO, Grand Island, N.Y.)). Monocytes (1 mL/well) are allowed to adhere to a 24-well Primaria Plate (coated tissue culture plates, available from VWR Scientific, South Plainfield, N.J.) for 2 hours (37° C., 5% $CO_2$), after which time non-adherent cells are removed by gentle washing.

Incubation

Compounds are dissolved in DMSO. Each compound is tested at 4 concentrations. Fresh media (HBSS) (1.0 mL) and compound (10 μL) or DMSO control is added to each well. After 1 hour at 37° C., LPS (10 ng/mL final concentration) is added to appropriate wells. Plates are incubated overnight at 37° C. At the end of the incubation period, 250 μL of each culture supernatant is removed and duplicate 10 μL samples are tested at a 1:20 dilution for TNF activity by ELISA (available from Quantikine, R&D Operations, Minneapolis, Minn.) according to the manufacturer's instructions.

TNF is determined by interpolating the average absorbance onto a standard curve. Percent inhibition is determined by the following equation: $(-[\text{pg/mL TNF experimental/pg/mL TNF DMSO control}]-1) \times 100$. $IC_{50}$ is determined by linear regression of drug concentration plotted against inhibition and interpolation of the x value at Y=50 using Biostat Linear Regression Program (available from Digital, Inc., Boston, Mass.).

For administration to humans to inhibit TNF in the treatment or alleviation of inflammatory conditions or disease, including but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, graft versus host disease and cachexia associated with AIDS or cancer, oral dosages of the compounds are generally in the range of from 0.1–500 mg daily for an average adult patient (70 kg). Thus for a typical adult patient, individual tablets or capsules contain from 0.1 to 50 mg of active compound, in a suitable pharmaceutically acceptable vehicle or carrier. Tablets or capsules can be given in multiple dosages to meet the dosage requirement. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in, the form of a sterile aqueous solution which may contain other substances; for example, enough salts or glucose to make the solution isotonic for intravenous administration. For topical administration, they are best used in the form of solutions, lotions, ointments, salves and the like.

The following examples illustrate the synthesis of certain compounds used in the present invention. The following examples combined with the synthetic methodologies described above enable those skilled in the art to make the compounds used in the present invention.

EXAMPLE 1

3-(3-Cyclopentyloxy-4-methoxy)phenyl-2-isoxazoline-5-hydroxamic Acid

To a solution of sodium methoxide, prepared from 97 mg (4.2 mmol) of sodium and 10 mL of methanol, was added 146 mg (2.1 mmol) of hydroxylamine hydrochloride in a solution of 3 mL of methanol followed by 500 mg (1.5 mmol) of the compound of Preparation 10. After stirring for about 16 h at RT, the solvent was evaporated and the residue was dissolved in 50 mL of water and washed with ether (2×50 mL). The aqueous layer was acidified to pH 1 with aqueous HCl solution and the precipitate (231 mg) was filtered and recrystallized twice from $CH_2Cl_2$/EtOAc to give 52 mg of the title compound, mp 167–168° C. $^1$H NMR (DMSO-$d_6$): δ 1.54–1.92 (8H, m), 3.48–3.67 (2H, m), 3.78 (3H, s), 4.79–4.85 (1H, m), 4.95 (1H, t, J=8), 6.99 (1H, d, J=9), 7.17 (1H, d, J=9), 7.23 (1H, s), 9.03 (1H, s); Anal. Calc'd. for $C_{16}H_{20}N_2O_5$: C, 59.99; H, 6.29; N, 8.74. Found: C, 59.82; H, 6.05; N, 8.65.

EXAMPLES 2–16

The following compounds having the formula shown below were prepared substantially according to the procedure of Example 1 substituting the indicated ester for that of the ester of Preparation 10. In the case of Example 5, N-methyl-hydroxylamine hydrochloride was substituted for hydroxylamine hydrochloride.

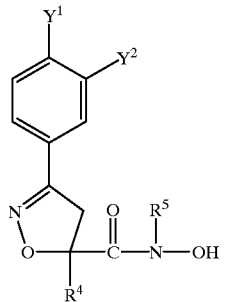

| Ex | $Y^1$ | $Y^2$ | $R^4$ | $R^5$ | Ester | M.P. (° C.) | Data |
|---|---|---|---|---|---|---|---|
| 2 | —OMe | —O(CH$_2$)$_5$Ph | H | H | Cmpd. of Prep 8 | 130–132 | Anal. Calc'd for $C_{22}H_{26}N_2O_5$: C, 66.32; H, 6.58; N, 7.03. Found: C, 66.23; H, 6.50; N, 6.94 |
| 3 | —OMe | —O(CH$_2$)$_5$Ph | Et | H | Cmpd. of Prep. 9 | 169–171 | Anal. Calc'd for $C_{24}H_{30}N_2O_5$ · ¼ $H_2O$: C, 66.82; H, 7.07; N, 6.49. Found: C, 67.13; H, 7.03; N, 6.15 |

-continued

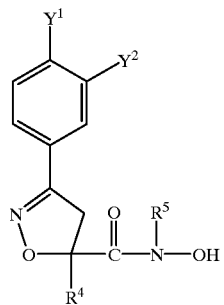

| Ex | Y¹ | Y² | R⁴ | R⁵ | Ester | M.P. (° C.) | Data |
|---|---|---|---|---|---|---|---|
| 4 | —OMe | —O-cyclopentyl | Me | H | Cmpd. of Prep. 12 | 171–173 | Anal. Calc'd for $C_{17}H_{22}N_2O_5 \cdot \frac{1}{2}H_2O$: C, 59.41; H, 6.70; N, 8.15. Found: C, 59.78; H, 6.38; N, 8.27 |
| 5 | —OMe | —O-cyclopentyl | H | Me | Cmpd. of Prep. 11 | 146–148 | Anal. Calc'd for $C_{17}H_{22}N_2O_5$: C, 61.07; H, 6.63; N, 8.38. Found: C, 60.87; H, 6.52; N, 8.45 |
| 6 | —OMe | —OMe | H | H | Cmpd. of Prep. 22 | 180–182 | Anal. Calc'd for $C_{12}H_{14}N_2O_5$: C, 54.13; H, 5.30; N, 10.52. Found: C, 54.03; H, 5.12; N, 10.60 |
| 7 | —OMe | —OCH₂Ph | H | H | Cmpd. of Prep. 23 | 166–168 | Anal. Calc'd for $C_{18}H_{18}N_2O_5$: C, 63.15; H, 5.30; H, 8.18. Found: C, 63.32; H, 5.37; H, 8.09 |
| 8 | quinolin-2-ylmethoxy | H | H | H | Cmpd. of Prep. 24 | — | ¹H NMR (DMSO-d₆): δ 3.48–3.68 (2H, m), 4.95 (1H, t, J = 8), 5.43 (2H, s), 7.15 (2H, d, J = 9), 7.59–7.69 (4H, m), 7.80 (1H, t, J = 8), 8.01 (2H, t, J = 7), 8.42 (1H, d, J = 9), 9.04 (1H, s), 10.99 (1H, s). MS (m/e): 363 (M⁺) |
| 9 | —OCH₂Ph | H | H | H | Cmpd. of Prep. 25 | 190–192 | ¹H NMR (DMSO-d₆): d 3.44–3.63 (2H, m), 4.94 (1H, t, J = 8), 5.15 (2H, s), 7.08 (2H, d, J = 8), 7.32–7.46 (5H, m), 7.62 (2H, d, J = 8), 9.03 (1H, s); MS (m/e): 313 (M⁺ + 1) |

-continued

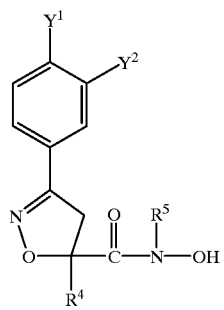

| Ex | Y$^1$ | Y$^2$ | R$^4$ | R$^5$ | Ester | M.P. (° C.) | Data |
|---|---|---|---|---|---|---|---|
| 10 | H | —O—⟨cyclopentyl⟩ | H | H | Cmpd. of Prep. 13 | 151–153 | Anal. Calc'd for C$_{15}$H$_{18}$N$_2$O$_4$: C, 62.06; H, 6.25; N, 9.65. Found: C, 62.00; H, 6.15; N, 9.36 |
| 11 | —O—⟨cyclopentyl⟩ | —OMe | H | H | Cmpd. of Prep. 14 | 136–138 | Anal. Calc'd for C$_{16}$H$_{20}$N$_2$O$_5$: C, 59.99; H, 6.29; N, 8.74. Found: C, 59.66; H, 6.21; N, 8.69 |
| 12 | H | H | H | H | Cmpd. of Prep. 17 | 166–168 | Anal. Calc'd for C$_{10}$H$_{10}$N$_2$O$_3$: C, 58.25; H, 4.89; N, 13.59. Found: C, 58.24; H, 4.49; N, 13.45 |
| 13 | OMe | —O—⟨cyclopentyl⟩ | Pr | H | Cmpd. of Prep. 18 | 154–157 | Anal. Calc'd for C$_{19}$H$_{26}$N$_2$O$_5$: C, 62.97; H, 7.23; N, 7.73. Found: C, 62.61; H, 7.19; N, 7.54. |
| 14 | OMe | —O—⟨cyclopentyl⟩ | Bu | H | Cmpd. of Prep. 19 | 135–138 | HRMS. Calc'd for C$_{20}$H$_{28}$N$_2$O$_5$: 376.19982. Found: 376.20104. |
| 15 | OMe | —O—⟨cyclopentyl⟩ | Ph | H | Cmpd. of Prep. 20 | 180–182 | Anal. Calc'd for C$_{22}$H$_{24}$N$_2$O$_5$: C, 66.65; H, 6.10; N, 7.07. Found: C, 66.32; H, 6.30; N, 7.12. |
| 16 | (structure shown below) | | | | Cmpd. of Prep. 21 | 111–133 | HRMS: Calc'd for C$_{19}$H$_{24}$N$_2$O$_5$: 360.1685; Found: 360.1684. |

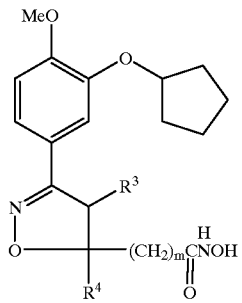

| Example | Ester Cmpd. of Prep. # | R³ | R⁴ | m | MP (° C.) | [α]²⁵_D | Anal. |
|---|---|---|---|---|---|---|---|
| 17 | 28 | H | H | 0 | 137–140° | +77° MeOH | Calc'd. for $C_{16}H_{20}N_2O_5$: C, 59.99; H, 6.29; N, 8.74. Found: C, 59.98; H, 6.62; N, 8.80. |
| 18 | 29 | H | H | 0 | 138–140° | −82° MeOH | Calc'd. for $C_{16}H_{20}N_2O_5$: C, 59.99; H, 6.29; N, 8.74. Found: C, 59.66; H, 6.44; N, 8.61. |
| 19 | 33 | H | H | 1 | 139–141° | racemic | Calc'd. for $C_{17}H_{22}N_2O_5 \cdot \frac{1}{4}H_2O$: C, 60.02; H, 6.64; N, 8.26. Found: C, 59.63; H, 6.48; N, 8.15. |
| 20[a] | 31 | Me | H | 0 | 184–186° | racemic | Calc'd. for $C_{17}H_{22}N_2O_5$: C, 61.01; H, 6.58; N, 8.38. Found: C, 61.08; H, 6.88; N, 8.04. |
| 21 | 39 | H | Me | 0 | 167–168° | +9°[b] $CHCl_3$ | Calc'd. for $C_{17}H_{22}N_2O_5 \cdot \frac{1}{4}H_2O$: C, 60.25; H, 6.69; N, 8.27. Found: C, 60.43; H, 6.70; N, 8.23. |
| 22 | 40 | H | Me | 0 | 153–155° | −14°[b] $CHCl_3$ | Calc'd. for $C_{17}H_{22}N_2O_5 \cdot \frac{1}{2}H_2O$: C, 59.41; H, 6.70; N, 8.15. Found: C, 59.64; H, 6.65; N, 8.03. |

[a] trans isomer
[b] These compounds are the resolved enantiomers of Example 4. The enantiomeric purity was 99% as determined by chiral HPLC using a Chrom Tech chiral column. Mobile phase: 98:2 10 mM ammonium acetate buffer, pH 4.1: 2-propanol; flow rate: 1 mL/min; detection: 230 nM; temperature: ambient; injection volume: 20 μL.

EXAMPLE 23

(+)-5-Hydroxymethyl-3-[4-methoxy-3-(5-phenylpentyloxy)]phenyl-2-isoxazoline

To a solution of 300 mg (0.617) of (S)-(−)-(N-α-methylbenzyl)-3-[4-methoxy-3-(5-phenylpentyloxy)]phenyl-2-isoxazoline-5-carboxamide (less polar diastereomer) in 10 ml of dry THF chilled to about −78° C. was added dropwise 1.85 ml (1.85 mmol) of 1M diisobutylaluminum hydride solution in hexane. After stirring for 20 min at about −78° C., the mixture was allowed to warm to about −20° C. and was quenched with 4 ml of aqueous 1N HCl solution. The mixture was concentrated, dissolved in 30 ml of EtOAc, washed with water (2×30 ml), dried ($MgSO_4$), and evaporated to 200 mg of a brown oil.

A solution of 184 mg of the oil above in 3 ml of MeOH was treated with 19 mg (0.50 mmol) of sodium borohydride, and the mixture was allowed to stir at RT for about 16 h. The mixture was quenched with aqueous 1N HCl solution and was partially evaporated to remove MeOH. The residue was extracted with EtOAc (1×50 ml) and the organic layer was separated, washed with water, dried ($MgSO_4$), and evaporated to a brown oil. Purification by flash chromatography (10 g of silica gel) using a EtOAc-hexane (2:3) eluant afford 96 mg of the title compound as an oil. ¹H NMR ($CDCl_3$): δ 1.46–1.92 (6H, m), 2.62 (3H, t, J=8), 3.18–3.39 (2H, m), 3.63–3.90 (2H, m), 3.86 (3H, s), 4.80–4.85 (1H, m), 6.83 (1H, d, J=8), 7.02 (1H, dd, J=8, 2), 7.12–7.33 (6H, m), MS (m/e): 370 (M⁺+1). $[\alpha]_D$+58.0°. ($CHCl_3$).

EXAMPLE 24

(+)-5-Hydroxymethyl-3-[4-methoxy-3-(5-phenylpentyloxy)]phenyl-5-methyl-2-isoxazoline A solution of 200 mg (0.524 mmol) of 3-[4-methoxy-3-(5-phenylpentyloxy)]phenyl-5-methyl-2-isoxazoline-5-carboxaldehyde in 4 ml of MeOH was treated with 18 mg (0.524 mmol) of sodium borohydride and the mixture was stirred for about 16 h at RT. The mixture was quenched with aqueous 1N HCl solution and was partially evaporated to remove MeOH. The residue was diluted with 50 ml of water, extracted with EtOAc (2×50 ml), dried ($MgSO_4$), and evaporated to 194 mg of an oil. Crystallization of the oil from hexane-ether (3:1) afforded 131 mg of the title compound, mp 76–78° C. $[\alpha]_D$+34.70° ($CHCl_3$). Anal. Calc'd for $C_{23}H_{29}NO_4 \cdot \frac{1}{4}H_2O$: C, 71.14; H, 7.60; N. 3.61. Found: C, 71.51; H, 7.72; N, 3.71.

PREPARATION 1

4-Methoxy-3-(5-phenylpentyloxy)benzaldehyde Oxime

A mixture of 25.0 g (0.164 mol) of isovanillin, 26.9 g (0.164 mol) of 5-phenyl-1-pentanol, 64.5 g (0.246 mol) of triphenylphosphine and 250 mL of THF was treated dropwise with 42.8 g (0.246 mol) of diethyl azodicarboxylate. The mixture was heated to about 90° C. for about 6 hrs and then stirred overnight at RT. The solvent was evaporated and the residue was diluted with 500 mL of EtOAc, washed with water (1×400 mL), 1 N NaOH solution (2×400 mL), brine (1×400 mL), dried (MgSO$_4$), and evaporated to 119 g of a brown oil. Purification by flash chromatography (750 g of silica gel) using an EtOAc-hexane (3:7) eluant afforded 29.8 g (61%) of an oil. $^1$H NMR (CDCl$_3$): δ 1.42–1.92 (6H, m), 2.61 (2H, t, J=7), 3.91 (3H, s), 4.03 (2H, t, J=7), 6.91 (1H, d, J=8), 7.10–7.40 (m, 7H), 9.77 (s, 1H).

To a solution of 29.8 g (0.100 mol) of the above aldehyde in 300 mL of 95% ethanol was added 13.7 g (0.197 mol) of hydroxylamine hydrochloride in 100 mL of water followed by 16.6 g (0.197 mol) of sodium bicarbonate in small portions (gas evolution!). The mixture was stirred for about 4 h at RT and the ethanol was removed by evaporation. The residue was diluted with 250 mL of water and extracted with EtOAc (2×200 mL). The combined extracts were dried (MgSO$_4$) and evaporated to a yellow oil which was crystallized from hexane/ether to afford 15.0 g of the title compound, mp 65–67° C. $^1$H NMR (CDCl$_3$):δ 1.46–1.93 (6H, m), 2.62 (2H, t, J=7), 3.88 (3H, s), 4.02 (2H, t, J=7), 6.99–7.62 (m, 6H), 7.49 (1H, s), 8.04 (1H, s).

An additional 2.00 g of product was obtained as a second crop from the filtrate, mp 67–69° C. Evaporation of the filtrate and purification of the residue by flash chromatography using an EtOAc-hexane (2:3) eluant also provided an additional 4.18 g of product, mp 64–66° C.

PREPARATIONS 2–4

The following compounds having the formula shown below were prepared, substantially according to the procedure of Preparation 1, substituting the indicated phenol for isovanillin and the indicated alcohol for 5-phenyl-1-pentanol. Compounds that were oils were purified by flash chromatography.

| Prep # | Y$^1$ | Y$^2$ | Phenol | Alcohol | M.P.(° C.) | $^1$H NMR (CDCl$_3$) δ: |
|---|---|---|---|---|---|---|
| 2 | —OMe | —O-cyclopentyl | isovanillin | cyclopentanol | oil | 1.50–2.02 (8H, m), 3.94 (3H, s), 4.62–4.80 (1H, m), 6.91 (1H, d, J = 8), 6.97 (1H, dd, J = 8 and 1), 7.17 (1H, d, J = 1), 8.02 (1H, s), 8.16 (1H, s) |
| 3 | H | —O-cyclopentyl | m-hydroxy-benzaldehyde | cyclopentanol | oil | 1.50–1.95 (8H, m), 4.70–4.78 (1H, m), 6.88 (1H, dd, J = 3, 8), 7.05–7.28 (3H, m), 8.09 (1H, s), 8.43 (1H, s) |
| 4 | —O-cyclopentyl | —OMe | vanillin | cyclopentanol | 110–111 | 1.55–2.02 (8H, m), 3.88 (3H, s), 4.78–4.88 (1H, m), 6.86 (1H, d, J = 8), 7.01 (1H, dd, J = 2, 8), 7.21 (1H, d, J = 2), 7.65 (1H, s), 8.07 (1H, s) |

PREPARATIONS 5–6

The following compounds having the formula shown below were prepared by condensation of the indicated aldehyde with hydroxylamine hydrochloride, substantially according to the procedure of Preparation 1.

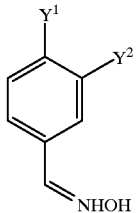

| Prep # | $Y^1$ | $Y^2$ | Aldehyde | M.P.(° C.) | $^1$H NMR (DMSO-$d_6$) δ: |
|---|---|---|---|---|---|
| 5 | —OMe | —OH | isovanillin | 146–148 | 3.77 (3H, s), 6.92 (2H, s), 7.08 (1H, s), 7.96 (1H, s), 9.16 (1H, s), 10.90 (1H, s) |
| 6 | —OH | H | p-hydroxy-benzaldehyde | 115–118 | 6.77 (2H, d, J = 9), 7.40 (2H, d, J = 9), 8.00 (1H, s), 9.74 (1H, s), 10.83 (1H, s) |

PREPARATION 7

Ethyl 2-Methylenebutyrate

A mixture of 5.0 g (0.019 mol) of triethyl 2-phosphonobutyrate, 5.5 g (0.039 mol) of $K_2CO_3$, 6.2 g (0.076 mol) of 37% aqueous formaldehyde solution, and 15 mL of water was heated to about 80° C. for about 45 min. After cooling to RT, 75 mL of ether was added and the organic layer was separated, washed with brine (1×20 mL), dried (MgSO$_4$), and filtered. The ether was carefully removed by distillation, leaving behind 2.1 g (87%) of the title compound as a clear oil which was used directly without further purification. $^1$H NMR (CDCl$_3$): δ 1.01 (3H, t, J=7), 1.24 (3H, t, J=7), 2.26 (2H, q, J=7), 4.14 (2H, q, J=7), 5.45 (1H, s), 6.06 (1H, s).

PREPARATION 8

3-[4-Methoxy-3-(5-phenylpentyloxy)]phenyl-2-isoxazoline-5-carboxylic Acid Ethyl Ester To a mixture of 1.28 g (9.57 mmol) of N-chlorosuccinimide, 200 µl of pyridine, and 200 mL of CH$_2$Cl$_2$ was added 2.00 g (6.38 mmol) of the compound of Preparation 1 in a solution of 15 mL of CH$_2$Cl$_2$. An exotherm was observed after about 10 min and following about 2 h of stirring at RT, 644 mg (698 µl, 6.38 mmol) of ethyl acrylate was added followed by 966 mg (1.33 ml, 9.57 mmol) of triethylamine. After the exotherm subsided, the mixture was stirred for about 2 h at RT. The mixture was diluted with 250 mL of CH$_2$Cl$_2$ and washed with aqueous 1N HCl solution, sat'd. aqueous NaHCO$_3$ solution, dried (Na$_2$SO$_4$), and evaporated to an oil. Purification by flash chromatography (100 g of a silica gel) using an EtOAc-hexane (2:3) eluant afforded 1.82 g (69%) of the title compound as an oil. $^1$H NMR (CDCl$_3$): δ 1.29 (3H, t, J=7), 1.40–1.91 (6H, m), 2.60 (2H, t, J=7), 3.55–3.58 (2H, m), 3.95 (3H, s), 3.99 (2H, t, J=7), 4.22 (2H, q, J=7), 5.05–5.12 (1H, m), 6.79 (1H, d, J=8), 6.95–7.31 (7H, m).

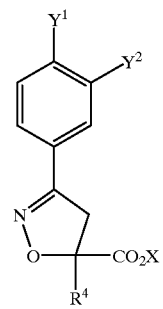

| Prep # | $Y^1$ | $Y^2$ | $R^4$ | X | Oxime | Olefin | M.P. (° C.) | $^1$H NMR (CDCl$_3$) δ or Elemental Analysis: |
|---|---|---|---|---|---|---|---|---|
| 9 | —OMe | O(CH$_2$)$_5$-Ph | Et | Et | Compound of Preparation 1 | Compound of Preparation 7 | oil | 0.98 (3H, t, J = 7), 1.30 (3H, t, J = 7), 1.48–2.03 (8H, m), 2.62 (2H, t, J = 7), 3.18 (1H, d, J = 17), 3.76 (1H, d, J = 17), 3.86 (3H, s), 4.01 (2H, q, J = 7), |

-continued

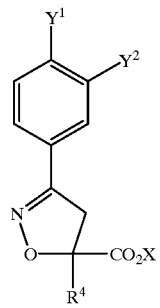

| Prep # | Y¹ | Y² | R⁴ | X | Oxime | Olefin | M.P. (° C.) | ¹H NMR (CDCl₃) δ or Elemental Analysis: |
|---|---|---|---|---|---|---|---|---|
| 10 | —OMe | —O-cyclopentyl | H | Et | Compound of Preparation 2 | Ethyl acrylate | oil | 6.82 (1H, d, J = 8), 7.01 (1H, dd, J = 2, 8), 7.15–733 (6H, m) 1.27 (3H, t, J = 7), 1.45–2.00 (8H, m), 3.56 (2H, d, J = 10), 3.82 (3H, s), 4.22 (2H, q, J = 7), 4.72–4.80 (1H, m), 5.09 (1H, t, J = 10), 6.78 (1H, d, J = 8), 6.98 (1H, d, J = 8), 7.32 (1H, s) |
| 11 | —OMe | —O-cyclopentyl | H | Me | Compound of Preparation 2 | Methyl acrylate | 101–102 | 1.45–2.00 (8H, m), 3.56 (2H, d, J = 10), 3.82 (3H, s), 3.87 (3H, s), 5.16 (1H, t, J = 10), 6.82 (1H, d, J = 8), 7.03 (1H, dd, J = 2, 8), 7.37 (1H, d, J = 2) |
| 12 | —OMe | —O-cyclopentyl | Me | Et | Compound of Preparation 2 | Ethyl methacrylate | 77–79 | 1.25 (3H, t, J = 7), 1.50–2.00 (8H, m), 1.63 (3H, s), 3.11 (1H, d, J = 17), 3.78 (1H, d, J = 17), 3.91 (3H, s), 4.18 (2H, q, J = 7), 4.68–4.77 (1H, m), 6.75 (1H, d, J = 8), 6.92 (1H, dd, J = 8, 2), 7.27 (1H, d, J = 2) |
| 13 | H | —O-cyclopentyl | H | Me | Compound of Preparation 3 | Methyl acrylate | oil | 1.45–1.95 (8H, m), 3.55–3.58 (2H, m), 3.85 (3H, s), 4.65–4.74 (1H, m), 5.09 (1H, t, J = 9), 6.85 (1H, dd, J = 2, 8), 7.07 (1H, d, J = 8), 7.12–7.22 (2H, m) |
| 14 | —O-cyclopentyl | OMe | H | Me | Compound of Preparation 4 | Methyl acrylate | oil | 1.45–1.95 (8H, m), 3.58–3.62 (2H, m), 3.79 (3H, s), 3.85 (3H, s), 4.65–4.74 (1H, m), 5.14 (1H, t, J = 9), 6.83 (1H, d, J = 9), 7.00 (1H, dd, J = 2, 8), 7.34 (1H, d, J = 2) |
| 15 | —OMe | —OH | H | Me | Compound of Preparation 5 | Methyl acrylate | 75–95 | 3.56–3.60 (2H, m), 3.79 (3H, s), 3.90 (3H, s), 5.12 (1H, t, J = 10), 5.66 (1H, s), 6.83 (1H, d, J = 9), 7.13 (1H, dd, J = 2, 9), 7.24 (1H, d, J = 2)* |
| 16 | —OH | H | H | Me | Compound of Preparation 6 | Methyl acrylate | 149–153 | 3.61–3.65 (2H, m), 3.83 (3H, s), 5.17 (1H, t, J = 9), 5.80 (1H, bd s), 6.88 (2H, d, J = 9), 7.56 (2H, d, J = 9) |
| 17 | H | H | H | Et | Benzaldehyde oxime | Ethyl acrylate | 40–41 | 1.50 (3H, t, J = 7) 3.60–3.65 (2H, m), 4.26 (2H, q, J = 7) 5.15 (1H, t, J = 9), 7.37–7.42 (3H, m), 7.64–7.70 (2H, m), |
| 18 | OMe | —O-cyclopentyl | Pr | Et | Compound of Preparation 2 | Compound of Prep. 34 | oil | 0.94 (3H, t, J = 8), 1.30 (3H, t, J = 8), 1.32–1.99 (12 H, m), 3.20 (1H, d, J = 17), 3.76 (1H, d, J = 17), 3.85 (3H, s), 4.18–4.32 (2H, m), 4.72–4.82 (1H, m), 6.82 (1H, d, J = 8), 7.00 (1H, dd, J = 2 and 8), 7.34 (1H, d, J = 2) |
| 19 | OMe | —O-cyclopentyl | Bu | Et | Compound of Preparation 2 | Compound of Prep. 35 | 53–36 | 0.90 (3H, t, J = 8), 1.30 (3H, t, J = 8), 1.22–1.98 (14H, m), 3.20 (1H, d, J = 17), 3.78 (1H, d, J = 17), 3.86 (3H, s), 4.20–4.29 (2H, m), 4.75–4.85 (1H, m), 6.82 (1H, d, J = 8), 7.01 (1H, dd, J = 2 and 8), 7.34 (1H, d, J = 2) |
| 20 | OMe | —O-cyclopentyl | Ph | Et | Compound of Preparation 2 | Compound of Prep. 36 | 98–100 | Anal. Calc'd for $C_{24}H_{27}NO_5$: C, 70.39; H, 6.65; N, 3.42. Found: C, 70.30; H, 6.81; N, 3.56 |

-continued

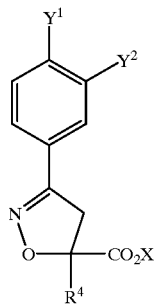

| Prep # | $Y^1$ | $Y^2$ | $R^4$ | X | Oxime | Olefin | M.P. (° C.) | $^1$H NMR (CDCl$_3$) δ or Elemental Analysis: |
|---|---|---|---|---|---|---|---|---|
| 21 | MeO | O-cyclopentyl | | | Compound of Preparation 2 | Methyl 1-cyclo-pentenoate | oil | 1.60–2.37 (14H, m), 3.79 (3H, s), 3.86 (3H, s), 4.21 (1H, dd, J = 3 and 7), 4.75–4.80 (1H, m), 6.82 (1H, d, J = 9), 7.05 (1H, dd, J = 2 and 9), 7.34 (1H, J = 2) |

*The NMR shows a contaminant which is most likely a product resulting from chlorination of the aromatic ring.

PREPARATION 22

3-(3,4-Dimethoxyphenyl)-2-isoxazoline-5-carboxylic Acid Methyl Ester

To a solution of 1.5 g (6.00 mmol) of the compound of Preparation 15 in 25 mL of DMF was added 910 mg of K$_2$CO$_3$ (6.60 mmol) and 0.41 mL (940 mg, 6.6 mmol) of methyl iodide. The mixture was heated to about 50° C. and the progress of the reaction was monitored by TLC. Additional 0.4 mL portions of methyl iodide were added at about 1 and 2 h, respectively. After about 2 h of additional heating, the reaction was cooled, diluted with 250 mL of water, extracted with EtOAc (3×100 mL), dried (MgSO$_4$), and evaporated to an oil. Purification by flash chromatography using an EtOAc-hexane (1:3) eluant afforded 270 mg of the title compound, mp 106–108° C. $^1$H NMR (CDCl$_3$): δ 3.59–3.63 (2H, m), 3.79 (3H, s), 3.89 (3H, s), 5.15 (1H, t, J=8), 6.83 (1H, d, J=8), 7.03 (1H, dd, J=2, 8), 7.37 (1H, d, J=8); MS (m/e): 266 (M$^+$+1).

PREPARATIONS 23–25

The following compounds having the formula shown below were prepared, substantially according to the procedure of Preparation 22, substituting the indicated phenol for that of Preparation 15 and the indicated alkylating agent for methyl iodide.

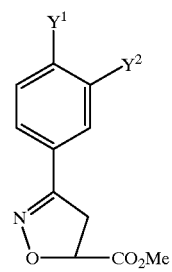

| Prep # | $Y^1$ | $Y^2$ | Phenol | Alkylating Agent | M.P.(° C.) | Data |
|---|---|---|---|---|---|---|
| 23 | OMe | OBn | Cmpd of Prep 15 | PhCH$_2$Br | 183–185 | $^1$H NMR (CDCl$_3$): δ 3.54–3.58 (2H,m), 3.79 (3H,s), 3,89 |

-continued

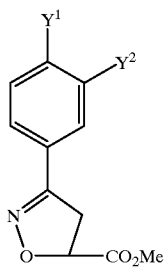

| Prep # | Y¹ | Y² | Phenol | Alkylating Agent | M.P.(° C.) | Data |
|---|---|---|---|---|---|---|
| 24 | quinolin-2-yl-CH₂O— | H | Cmpd of Prep 16 | quinolin-2-yl-CH₂Cl | 112–113 | (3H,s), 5.10–5.26 (1H,m) 5.13 (2H,s), 6.86 (1H, d, J = 9), 7.06 (1H, dd, J = 2,8), 7.32–7.40 (6H,m); MS (m/e): 342 (M⁺ + 1) ¹H NMR (CDCl₃): δ 3.56–3.59 (2H, m), 3.78 (3H, s), 5.12 (1H, t, J = 8), 5.34 (2H, s), 7.02 (2H, d, J = 9), 7.54–7.82 (6H, m), 8.06 (1H, d, J = 8), 8.17 (1H, d, J = 8); MS (m/e): 363 (M⁺ +1) |
| 25 | —OCH₂Ph | H | Cmpd of Prep 16 | PhCH₂Br | 127–128 | Anal. Calc'd for C₁₈H₁₇NO₄: C, 69.43; H, 5.50; N, 4.50. Found: C, 69.18; H, 5.31; N, 4.59 |

PREPARATION 26

[3aR-(3aα,6α,7aβ]-Hexahydro-8,8-dimethyl-1-(1-oxo-2-propenyl)-3H-3a, 6-methano-2,1-benzisothiazole 2,2-Dioxide The title compound was prepared according to the method of Curran and Heffner (Curran, D. P., Heffner, T. A., *J. Org. Chem.*, 1990, 55, 4585) starting with (+)-L-2,10-camphor sultam, which was purchased from Fluka.

Into a 1L 3-neck round bottom flask fitted with reflux condenser, N₂ inlet, rubber septum and glass stopper was placed 4.03 g (0.084 mol) of 50% NaH dispersion, 400 mL of toluene, and 12.0 g (0.056 mol) of (+)-10,2-camphor sultam. After stirring for 1 h. at RT, 594 mg (0.006 mol) of CuCl followed by 9.10 mL (0.056 mol) of acryloyl chloride were added and stirring was continued overnight at RT. The mixture was then treated with 15 mL of water, evaporated, diluted with water (200 mL), and extracted with EtOAc (3×200 mL). The combined extracts were dried (MgSO₄) and evaporated to a solid. Purification by flash chromatography (1 kg of silica gel) using a 3:7 EtOAc-hexane eluant afforded a white solid which was triturated with ether to provide 7.4 g of the title compound, mp 179–182° C.

PREPARATION 27

[3aS-(3aα,6α,7aβ]-Hexahydro-8,8-dimethyl-1-(1-oxo-2-propenyl)-3H-3a,6-methano-2,1-benzisothiazole 2,2-Dioxide The title compound was prepared according to the procedure of Preparation 26, however, starting with (−)-D-2,10-camphor sultam, which was purchased from Fluka.

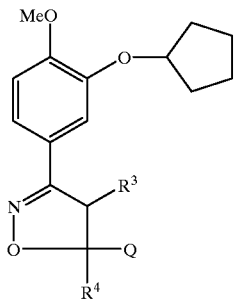

| Prep. | R³ | R⁴ | Q | Olefin | MP (° C.) | $[\alpha]^{25}_D$ CHCl₃ | Data |
|---|---|---|---|---|---|---|---|
| 28[a] | H | H | (acyl-sultam group, see structure) | Compound of Prep. 26 | foam | +187° | ¹H-NMR(CDCl₃);δ 0.97 (3H, s), 1.19 (3H, s), 1.28–2.22 (15H, m), 3.41–3.95 (5H, m), 3.85 (3H, s), 4.74–4.82 (1H, m), 5.63 (1H, dd, J = 8, 10), 6.80 (1H, d, J = 8), 7.02 (1H, dd, J = 2, 8), 7.33 (1H, d, J = 2). |
| 29[a] | H | H | (acyl-sultam group, see structure) | Compound of Prep. 27 | foam | +46° | ¹H-NMR(CDCl₃); δ 0.94 (3H, s), 1.17 (3H, s), 1.25–2.21 (15H, m), 3.39–3.93 (5H, m), 3.83 (3H, s), 4.73–4.81 (1H, m), 5.61 (1H, dd, J = 8, 10), 6.79 (1H, d, J = 8), 7.01 (1H, dd, J = 2, 8), 7.32 (1H, d, J = 2). |
| 30 | H | H | (CH₂)₂OH | CH₂=CH(CH₂)₂OH | 89–91 | racemic | Anal. Calc'd. for C₁₇H₂₃NO₄: C, 66.86; H, 7.59; N, 4.59. Found: C, 66.71; H, 7.77; N, 4.64. |
| 31[b] | H | Me | CO₂Me | ethyl crotonate | oil | racemic | ¹H-NMR(CDCl₃): 1.40–2.05 (8H, m), 1.43 (3H, d, J = 7), 3.69 (3H, s), 3.84 (3H, s), 4.01 (1H, d, J = 7), 4.74–4.82 (1H, m), 4.95–5.06 (1H, m), 6.79 (1H, d, J = 8), 7.05 (1H, dd, J = 2, 8), 7.31 (1H, d, J = 2). |

[a] less polar diastereomer (R_f 0.61; 1:1 ether-toluene);
[b] trans stereochemistry

PREPARATION 32

3-(3-Cyclopentyloxy-4-methoxy)phenyl-2-isoxazoline-5-acetic Acid

To a solution of 1.85 g (6.06 mmol) of the compound of Preparation 30 in 50 mL of acetone chilled to about 0° C. in an ice bath was added dropwise 9.70 mL (12.1 mmol) of a 1.25 M solution of Jones reagent. The ice bath was allowed to melt, and after about 4 h. of stirring an additional 2.00 mL of Jones reagent was added and stirring was continued overnight. Excess reagent was quenched by the addition of 10 mL of isopropanol, and the solids were removed by filtration. The filtrate was concentrated and the residue was taken up in 150 mL of EtOAc, washed with water (2×100 mL), dried (MgSO₄), and evaporated to a yellow oil. Crystallization from ether-hexane gave 1.06 g of the title compound, mp 123–126° C. ¹H-NMR (CDCl₃): δ 1.55–2.06 (8H, m), 2.66–3.59 (4H, m), 3.87 (3H, s), 4.78–4.87 (1H, m), 5.02–5.15 (1H, m) 6.84 (1H, d, J=8), 7.02 (1H, dd, J=2, 8), 7.37 (1H, d, J=2).

PREPARATION 33

3-(3-Cyclopentyloxy-4-methoxy)phenyl-2-isoxazoline-5-acetic Acid Methyl Ester A solution of 530 mg of the compound of Preparation 32 in 5 mL of MeOH was saturated with HCl gas and the mixture was stirred for about 3 h. at RT protected from atmospheric moisture with a CaCl₂ tube. The mixture was concentrated and the residue was taken up in 50 mL of EtOAc, washed with saturated aqueous NaHCO₃ solution (2×50 mL), dried (MgSO₄), and evaporated to 530 mg of an oil. Purification by flash chromatography (25 g of silica gel) using a 2:3—EtOAc:hexane eluant gave an oil which was crystallized from hexane-ether to afford 323 mg of the title compound as a white solid, mp 78–80° C. Anal. Calc'd. for C₁₈H₂₃NO₅; C, 64.85; H, 6.95; N, 4.20. Found: C, 64.49; H, 7.08; N, 4.13.

PREPARATIONS 34–36

The following compounds having the formula shown below were prepared as oils substantially according to the procedure of Preparation 7 substituting the indicated ester for triethylphosphonobutyrate.

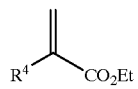

| Prep. # | R⁴ | Ester | $^1$H-NMR(CDCl$_3$):δ |
|---|---|---|---|
| 34 | Pr | triethyl phosphonopentanoate | 0.90 (3H, t, J = 7), 1.28 (3H, t, J = 7), 1.40–1.53 (2H, m), 2.25 (2H, dt, J = 1 and 7), 4.17 (2H, q, J = 7), 5.48 (1H, q, J = 1), 6.11 (1H, t, J = 1) |
| 35 | Bu | triethyl phosphonohexanoate | 0.90 (3H, t, J = 7), 1.29 (3H, t, J = 7), 1.26–1.48 (4H, m), 2.28 (2H, t, J = 7), 4.19 (2H, q, J = 7), 5.49 (1H, q, J = 1), 6.11 (1H, t, J = 1) |
| 36 | Ph | triethyl phosphonophenylacetate | 1.32 (3H, t, J = 7), 4.28 (2H, q, J = 7), 5.88 (1H, d, J = 1), 6.34 (1H, d, J = 1), 7.20–7.45 (5H, m) |

PREPARATIONS 37 and 38

Less Polar Diastereomer of N-[(S)-α-Methylbenzyl]-3-(3-cyclopentyloxy-4-methoxy)phenyl-5-methyl-2-isoxazoline-5-carboxamide (Preparation 37)

More Polar Diastereomer of N-[(S)-α-Methylbenzyl]-3-(3-Cyclopentyloxy-4-methoxy)phenyl-5-methyl-2-isoxazoline-5-carboxamide (Preparation 38)

A solution of 5.00 g (14 mmol) of the compound of Preparation 12 in 100 mL of absolute ethanol was treated with 2.36 g (42 mmol) of KOH and the mixture was stirred for about 4 hr at RT. An additional equivalent of KOH was added and stirring was continued for about 3 days. The mixture was concentrated, diluted with water, acidified with aqueous 1N HCl solution, and extracted with EtOAc (2×100 mL). The combined extracts were dried (MgSO$_4$), evaporated, and triturated with hexane-ether to give 3.46 g of 3-[3-cyclopentyloxy-4-methoxy]phenyl-5-methyl-2-isoxazoline-5-carboxylic acid, mp 153–154°.

A mixture of 3.00 g (94 mmol) of the above compound, 100 mL of benzene, and 2.46 mL (28.2 mmol) of oxalyl chloride was heated to reflux for about 3 hr. The mixture was concentrated, diluted with 100 mL of CH$_2$Cl$_2$, and treated with 2.42 mL (18.8 mmol) of S-(–)-α-methylbenzylamine. After stirring for about 16 hr at RT, the mixture was concentrated, diluted with 200 mL of EtOAc, washed with aqueous 1N HCl solution (2×100 mL), saturated aqueous NaHCO$_3$ solution (2×100 mL), dried (Na$_2$SO$_4$), and evaporated. The residual solid (5.76 g) was purified by flash chromatography over 600 g of silica gel using 15–20% ether-toluene as eluant. Following a 500 mL pre-fraction, 35 ml-fractions were collected. Fractions 59–68 were pooled and evaporated to give 630 mg of the compound of Preparation 37, mp 154–156° C.; R$_f$0.20, 20% ether-toluene. Anal. calculated for C$_{25}$H$_{30}$N$_2$O$_4$: C, 71.06; H, 7.16; N, 6.63. Found: C, 71.13; H, 7.42; N, 6.76.

Fractions 82–104 were pooled and concentrated to 720 mg of a white solid which was triturated with hexane-ether to give 596 mg of a white solid, mp 165–167° C. Recrystallization from ether-CH$_2$Cl$_2$ afforded 435 mg of the compound of Preparation 38, mp 167–168° C. An additional 1.03 g of the compound of Preparation 38, mp 166–167° C., was obtained by recrystallization (ether-CH$_2$Cl$_2$) of the combined evaporated residues of the mother liquor and Fractions 69–81. Anal. calculated for C$_{25}$H$_{30}$N$_2$O$_4$: C, 71.06; H, 7.16; N, 6.63. Found: C, 70.89; H, 7.40; N, 6.77.

PREPARATION 39

(+)-3-(3-Cyclopentyloxy-4-methoxy)phenyl-5-methyl-2-isoxazoline-5-carboxylic Acid Methyl Ester Into a flame-dried, 3-neck round-bottom flask under N$_2$ was placed a suspension of 549 mg (3.56 mmol) of 26% KH in mineral oil. After removal of the mineral oil by 2 successive hexane washes, the bare hydride was suspended in 35 mL of THF and a solution of 750 mg (1.78 mmol) of the compound of Preparation 37 in 35 mL of dry THF was added dropwise. After the bubbling subsided, 161 μl (2.67 mmol) of carbon disulfide was added. The mixture was stirred for about 16 hr at RT and was quenched by the addition of 6 mL of water. The THF was evaporated and the residue was diluted with saturated aqueous NaHCO$_3$ solution and washed with EtOAc (2×100 mL). The aqueous layer was acidified to pH 3 with aqueous 6N HCl solution, extracted with EtOAc (2×100 mL), dried (MgSO$_4$), and evaporated to 217 mg of an orange oil.

A solution of the above oil in 20 mL of MeOH was saturated with HCl gas and stirred for about 16 hr at RT. The mixture was concentrated, diluted with 50 mL of EtOAc, dried (MgSO$_4$), and evaporated to a yellow solid. Purification by flash chromatography over 12 g of silica gel using a 60% EtOAc-hexane eluant afforded 131 mg of the title compound after trituration in hexane-ether, mp 127–128° C. $[α]_D^{25}$+100° (c=0.64, CHCl$_3$). Anal calculated for C$_{18}$H$_{23}$NO$_5$.¼H$_2$O: C, 63.99; H, 7.01; N, 4.15. Found: C, 64.03; H, 6.96; N, 4.15.

PREPARATION 40

(–)-3-(3-Cyclopentyloxy-4-methoxy)phenyl-5-methyl-2-isoxazoline-5-carboxamide

The title compound was prepared substantially according to Procedure 39 substituting the compound of Preparation 38 for the compound of Preparation 37; mp 124–125° C.; $[α]_D^{25}$–101° (c=0.61, CHCl$_3$). Anal. calculated for C$_{18}$H$_{23}$NO$_5$. ¼H$_2$O: C, 63.99; H, 7.01; N, 4.15. Found: C, 64.04; H, 7.00; N, 4.17.

What is claimed is:

1. A method of inhibiting production of TNF (tumor necrosis factor) in a mammal in need thereof which method comprises administering to said mammal an effective amount of a compound selected from the group consisting of compounds of the formula (I)

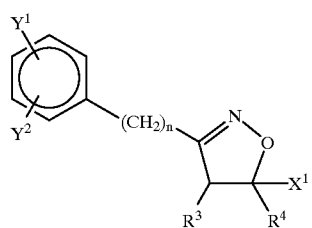

(I)

the racemic, racemic-diastereomeric mixtures and optical isomers of said compounds, and the pharmaceutically acceptable salts thereof, wherein $X^1$ is —$(CH_2)_q$OH, —CHOHR$^5$ or —$(CH_2)_m$CON(R$^6$)(OH);
  wherein q and m are each independently 0 or an integer from 1 to 5; R$^5$ is (C$_1$–C$_4$)alkyl; and R$^6$ is hydrogen or (C$_1$–C$_3$)alkyl;

n is 0, 1, 2 or 3;

$Y^1$ and $Y^2$ are independently selected from the group consisting of hydrogen, (C$_1$–C$_6$)alkyl, optionally substituted phenylalkyl having 1 to 6 carbons in the alkyl portion, optionally substituted phenoxyalkyl having 1 to 6 carbons in the alkyl portion, (C$_3$–C$_7$)cycloalkyl, difluoromethyl, trifluoromethyl, fluoro, chloro, bromo, iodo, —OR$^1$ and —OR$^2$;
  wherein the aromatic portion of the optionally substituted phenylalkyl, and the aromatic portion of the optionally substituted phenoxyalkyl are optionally independently substituted with (C$_1$–C$_4$)alkyl, (C$_1$–C$_4$)alkoxy, halogen or CF$_3$;

R$^1$ is (C$_1$–C$_5$)alkyl, phenylalkyl having one to four carbon atoms in the alkyl portion, fluoromethyl, difluoromethyl, trifluoromethyl, or —(CH$_2$)$_r$-quinoline wherein r is 0 or an integer from 1 to 5;

R$^2$ is (C$_1$–C$_3$)alkyl, (C$_3$–C$_7$)cycloalkyl, alkoxyalkyl having 3 to 7 carbons in the alkoxy portion and 2 to 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;
  wherein the aromatic portion of the optionally substituted phenylalkyl, the aromatic portion of the optionally substituted phenoxyalkyl and the optionally substituted indanyl are optionally substituted with (C$_1$–C$_4$)alkyl, (C$_1$–C$_4$)alkoxy, halogen or CF$_3$;

R$^3$ is hydrogen, (C$_1$–C$_3$)alkyl, fluoro(C$_1$–C$_3$)alkyl having 1 to 3 fluoro atoms, mono-hydroxyalkyl having 1 to 3 carbons or alkoxyalkyl having 1 to 3 carbons in the alkyl portion and 1 to 3 carbons in the alkoxy portion;

R$^4$ is hydrogen, (C$_1$–C$_5$)alkyl, fluoro(C$_1$–C$_5$)alkyl having 1 to 3 fluoro atoms, mono-hydroxyalkyl having 1 to 3 carbons, phenyl, alkoxyalkyl having 1 to 3 carbons in the alkyl portion and 1 to 3 carbons in the alkoxy portion, aminoalkyl having 1 to 3 carbons,

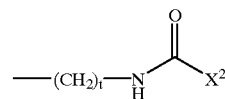

wherein X$^2$ is (C$_1$–C$_3$)alkyl and t is an integer from 1 to 3, N-alkylaminoalkyl having 1 to 3 carbons in the alkylamino portion and 1 to 3 carbons in the alkyl portion, (C$_3$–C$_7$)cycloalkyl or N,N-dialkylaminoalkyl having a total of 2 to 6 carbons in the dialkylamino portion and 1 to 3 carbons in the alkyl portion;

or R$^3$ and R$^4$ are taken together with the carbon atoms to which they are attached and form a carbocyclic ring having 4 to 7 carbon atoms.

2. A method of inhibiting production of TNF in a mammal in need thereof according to claim 1 wherein Y$^1$ is —OR$^1$ and is attached to the 4-position of the phenyl ring and Y$^2$ is —OR$^2$ and is attached to the 3-position of the phenyl ring.

3. A method of inhibiting production of TNF in a mammal in need thereof according to claim 2 wherein X$^1$ is —(CH$_2$)$_m$CON(R$^6$)(OH), R$^1$ is (C$_1$–C$_4$)alkyl, phenylalkyl having one to four carbon atoms in the alkyl portion or —(CH$_2$)$_r$-quinoline; and n is 0.

4. A method of inhibiting production of TNF in a mammal in need thereof according to claim 3 wherein R$^2$ is phenylalkyl having 1 to 6 carbons in the alkyl portion, (C$_3$–C$_7$)cycloalkyl or (C$_1$–C$_3$)alkyl and m is 0.

5. A method of inhibiting production of TNF in a mammal in need thereof according to claim 4 wherein R$^2$ is 5-phenylpentyl, benzyl, cyclopentyl or methyl.

6. A method of inhibiting production of TNF in a mammal in need thereof according to claim 5 wherein R$^3$ is hydrogen.

7. A method of inhibiting production of TNF in a mammal in need thereof according to claim 6 wherein R$^4$ is hydrogen or (C$_1$–C$_5$)alkyl.

8. A method of inhibiting production of TNF in a mammal in need thereof according to claim 7 wherein R$^6$ is hydrogen or (C$_1$–C$_3$)alkyl.

9. A method of inhibiting production of TNF in a mammal in need thereof according to claim 8 wherein R$^1$ is methyl; R$^2$ is cyclopentyl; R$^4$ is hydrogen; and R$^6$ is hydrogen.

10. A method of inhibiting production of TNF in a mammal in need thereof according to claim 9 wherein the levorotatory (negative rotation) enantiomer of the compound is used.

11. A method of inhibiting production of TNF in a mammal in need thereof according to claim 8 wherein R$^1$ is methyl; R$^2$ is cyclopentyl; R$^4$ is methyl; and R$^6$ is hydrogen.

12. A method of inhibiting production of TNF in a mammal in need thereof according to claim 11 wherein the levorotatory (negative rotation) enantiomer of the compound is used.

13. A method of inhibiting production of TNF in a mammal in need thereof according to claim 1 wherein X$^1$ is —(CH$_2$)$_q$OH, or —CH(OH)CH$_3$ wherein q is 0, 1 or 2; Y$^1$ is methoxy or —OCH$_2$-2-quinoline and is attached to the 4-position of the phenyl ring; R$^3$ is hydrogen, methyl or ethyl; n is 0; Y$^2$ is hydrogen, cyclopentyloxy or —O(CH$_2$)$_5$phenyl and is attached to the 3-position of the phenyl ring; and R$^4$ is hydrogen, methyl or ethyl.

14. A method of inhibiting production of TNF in a mammal in need thereof according to claim 1 wherein X$^1$ is —CONHOH; Y$^1$ is —OCH$_2$-2-quinoline and is attached to the 4-position of the phenyl ring; R$^3$ is hydrogen, methyl or ethyl; n is 0; Y$^2$ is hydrogen or —O(CH$_2$)$_5$phenyl and is attached to the 3-position of the phenyl ring; and R$^4$ is ethyl.

15. A method of treating or alleviating sepsis, septic shock, inflammatory bowel disease, tuberculosis, graft versus host disease or cachexia associated with AIDS or cancer in a mammal in need thereof which method comprises administering to said mammal an effective amount of a compound selected from the group consisting of compounds of the formula (I)

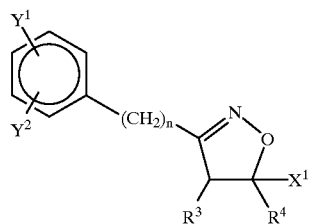

the racemic, racemic-diastereomeric mixtures and optical isomers of said compounds, and the pharmaceutically acceptable salts thereof, wherein $X^1$ is —$(CH_2)_q OH$, —$CHOHR^5$ or —$(CH_2)_m CON(R^6)(OH)$;
  wherein q and m are each independently 0 or an integer from 1 to 5; $R^5$ is $(C_1-C_4)$alkyl; and $R^6$ is hydrogen or $(C_1-C_3)$alkyl;

n is 0, 1, 2 or 3;

$Y^1$ and $Y^2$ are independently selected from the group consisting of hydrogen, $(C_1-C_6)$alkyl, optionally substituted phenylalkyl having 1 to 6 carbons in the alkyl portion, optionally substituted phenoxyalkyl having 1 to 6 carbons in the alkyl portion, $(C_3-C_7)$cycloalkyl, difluoromethyl, trifluoromethyl, fluoro, chloro, bromo, iodo, —$OR^1$ and —$OR^2$;
  wherein the aromatic portion of the optionally substituted phenylalkyl, and the aromatic portion of the optionally substituted phenoxyalkyl are optionally independently substituted with $(C_1-C_4)$alkyl, $(C_1-C_4)$alkoxy, halogen or $CF_3$;

$R^1$ is $(C_1-C_5)$alkyl, phenylalkyl having one to four carbon atoms in the alkyl portion, fluoromethyl, difluoromethyl, trifluoromethyl, or —$(CH_2)_r$-quinoline wherein r is 0 or an integer from 1 to 5;

$R^2$ is $(C_1-C_3)$alkyl, $(C_3-C_7)$cycloalkyl, alkoxyalkyl having 3 to 7 carbons in the alkoxy portion and 2 to 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;
  wherein the aromatic portion of the optionally substituted phenylalkyl, the aromatic portion of the optionally substituted phenoxyalkyl and the optionally substituted indanyl are optionally substituted with $(C_1-C_4)$alkyl, $(C_1-C_4)$alkoxy, halogen or $CF_3$;

$R^3$ is hydrogen, $(C_1-C_3)$alkyl, fluoro$(C_1-C_3)$alkyl having 1 to 3 fluoro atoms, mono-hydroxyalkyl having 1 to 3 carbons or alkoxyalkyl having 1 to 3 carbons in the alkyl portion and 1 to 3 carbons in the alkoxy portion;

$R^4$ is hydrogen, $(C_1-C_5)$alkyl, fluoro$(C_1-C_5)$alkyl having 1 to 3 fluoro atoms, mono-hydroxyalkyl having 1 to 3 carbons, phenyl, alkoxyalkyl having 1 to 3 carbons in the alkyl portion and 1 to 3 carbons in the alkoxy portion, aminoalkyl having 1 to 3 carbons,

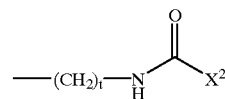

wherein $X^2$ is $(C_1-C_3)$alkyl and t is an integer from 1 to 3, N-alkylaminoalkyl having 1 to 3 carbons in the alkylamino portion and 1 to 3 carbons in the alkyl portion, $(C_3-C_7)$cycloalkyl or N,N-dialkylaminoalkyl having a total of 2 to 6 carbons in the dialkylamino portion and 1 to 3 carbons in the alkyl portion;

or $R^3$ and $R^4$ are taken together with the carbon atoms to which they are attached and form a carbocyclic ring having 4 to 7 carbon atoms.

16. A pharmaceutical composition comprising a pharmaceutically acceptable diluent or carrier and a tumor necrosis factor inhibiting amount of a compound selected from the group consisting of compounds of the formula (I)

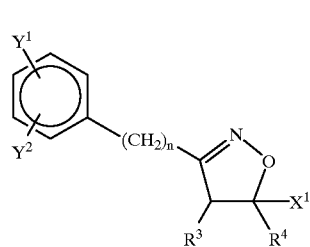

the racemic, racemic-diastereomeric mixtures and optical isomers of said compounds, and the pharmaceutically acceptable salts thereof, wherein $X^1$ is —$(CH_2)_q OH$, —$CHOHR^5$ or —$(CH_2)_m CON(R^6)(OH)$;
  wherein q and m are each independently 0 or an integer from 1 to 5; $R^5$ is $(C_1-C_4)$alkyl; and $R^6$ is hydrogen or $(C_1-C_3)$alkyl;

n is 0, 1, 2 or 3;

$Y^1$ and $Y^2$ are independently selected from the group consisting of hydrogen, $(C_1-C_6)$alkyl, optionally substituted phenylalkyl having 1 to 6 carbons in the alkyl portion, optionally substituted phenoxyalkyl having 1 to 6 carbons in the alkyl portion, $(C_3-C_7)$cycloalkyl, difluoromethyl, trifluoromethyl, fluoro, chloro, bromo, iodo, —$OR^1$ and —$OR^2$;
  wherein the aromatic portion of the optionally substituted phenylalkyl, and the aromatic portion of the optionally substituted phenoxyalkyl are optionally independently substituted with $(C_1-C_4)$alkyl, $(C_1-C_4)$alkoxy, halogen or $CF_3$;

$R^1$ is $(C_1-C_5)$alkyl, phenylalkyl having one to four carbon atoms in the alkyl portion, fluoromethyl, difluoromethyl, trifluoromethyl, or —$(CH_2)_r$-quinoline wherein r is 0 or an integer from 1 to 5;

$R^2$ is $(C_1-C_3)$alkyl, $(C_3-C_7)$cycloalkyl, alkoxyalkyl having 3 to 7 carbons in the alkoxy portion and 2 to 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;

wherein the aromatic portion of the optionally substituted phenylalkyl, the aromatic portion of the optionally substituted phenoxyalkyl and the optionally substituted indanyl are optionally substituted with $(C_1-C_4)$alkyl, $(C_1-C_4)$alkoxy, halogen or $CF_3$;

$R^3$ is hydrogen, $(C_1-C_3)$alkyl, fluoro$(C_1-C_3)$alkyl having 1 to 3 fluoro atoms, mono-hydroxyalkyl having 1 to 3 carbons or alkoxyalkyl having 1 to 3 carbons in the alkyl portion and 1 to 3 carbons in the alkoxy portion;

$R^4$ is hydrogen, $(C_1-C_5)$alkyl, fluoro$(C_1-C_5)$alkyl having 1 to 3 fluoro atoms, mono-hydroxyalkyl having 1 to 3 carbons, phenyl, alkoxyalkyl having 1 to 3 carbons in the alkyl portion and 1 to 3 carbons in the alkoxy portion, aminoalkyl having 1 to 3 carbons,

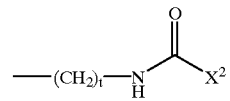

wherein $X^2$ is $(C_1-C_3)$alkyl and t is an integer from 1 to 3, N-alkylaminoalkyl having 1 to 3 carbons in the alkylamino portion and 1 to 3 carbons in the alkyl portion, $(C_3-C_7)$ cycloalkyl or N,N-dialkylaminoalkyl having a total of 2 to 6 carbons in the dialkylamino portion and 1 to 3 carbons in the alkyl portion;

or $R^3$ and $R^4$ are taken together with the carbon atoms to which they are attached and form a carbocyclic ring having 4 to 7 carbon atoms.

* * * * *